US007173160B2

(12) United States Patent
Maesen et al.

(10) Patent No.: US 7,173,160 B2
(45) Date of Patent: Feb. 6, 2007

(54) PROCESSES FOR CONCENTRATING HIGHER DIAMONDOIDS

(75) Inventors: Theo Maesen, Point Richmond, CA (US); Robert M. Carlson, Petaluma, CA (US); Jeremy E. Dahl, Palo Alto, CA (US); Shenggao Liu, Hercules, CA (US); Hye Kyung C. Timken, Albany, CA (US); Waqar R. Qureshi, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 607 days.

(21) Appl. No.: 10/622,185

(22) Filed: Jul. 16, 2003

(65) Prior Publication Data

US 2004/0054243 A1    Mar. 18, 2004

Related U.S. Application Data

(60) Provisional application No. 60/396,991, filed on Jul. 18, 2002.

(51) Int. Cl.
*C07C 13/28* (2006.01)
*C07C 7/148* (2006.01)
*C07C 7/00* (2006.01)
*C10G 47/00* (2006.01)

(52) U.S. Cl. ............... 585/352; 585/258; 585/800; 208/142; 208/107; 208/108; 208/109; 208/110; 208/112; 208/143; 208/144; 208/145; 208/49; 208/78; 208/111.01

(58) Field of Classification Search ............... 585/352, 585/258, 800; 208/142, 107, 108, 109, 110, 208/112, 143, 49, 144, 78, 145, 111.01
See application file for complete search history.

(56) References Cited

U.S. PATENT DOCUMENTS

| | | | |
|---|---|---|---|
| 3,852,207 A | 12/1974 | Stangeland et al. |
| 4,347,121 A | 8/1982 | Mayer et al. |
| 4,401,556 A | 8/1983 | Bezman et al. |
| 4,534,852 A | 8/1985 | Washecheck et al. |
| 4,556,646 A | 12/1985 | Bezman |
| 4,820,402 A | 4/1989 | Partridge et al. |
| 4,913,799 A | 4/1990 | Gortsema et al. |
| 4,956,747 A | 9/1990 | Beer et al. |
| 4,956,748 A | 9/1990 | Yamamoto |
| 4,956,749 A | 9/1990 | Chang |
| 4,982,049 A | 1/1991 | Alexander et al. |
| 5,019,665 A | 5/1991 | Partridge et al. |
| 5,059,567 A | 10/1991 | Linsten et al. |
| 5,073,530 A | 12/1991 | Bezman et al. |
| 5,080,776 A | 1/1992 | Partridge et al. |
| 5,114,563 A | 5/1992 | Lok et al. |
| 5,120,899 A | 6/1992 | Chen et al. |
| 5,198,203 A | 3/1993 | Kresge et al. |
| 5,246,689 A | 9/1993 | Beck et al. |
| 5,306,851 A | 4/1994 | Wu et al. |
| 5,334,368 A | 8/1994 | Beck et al. |
| 5,414,189 A | 5/1995 | Chen et al. |
| 5,439,860 A | 8/1995 | Habib et al. |
| 5,468,372 A | 11/1995 | Seamans et al. |
| 5,495,283 A | 2/1996 | Cowe |
| 5,498,812 A | 3/1996 | Bradway et al. |
| 5,925,235 A | 7/1999 | Habib |
| 6,013,239 A | 1/2000 | Chen et al. |
| 6,179,995 B1 | 1/2001 | Cash et al. |
| 6,534,437 B2 | 3/2003 | Eijsbouts et al. |
| 6,743,290 B2 | 6/2004 | Dahl et al. |
| 2002/0134301 A1 | 9/2002 | Dahl et al. |
| 2002/0137976 A1 | 9/2002 | Dahl et al. |
| 2002/0143217 A1 | 10/2002 | Dahl et al. |
| 2002/0143218 A1 | 10/2002 | Dahl et al. |
| 2002/0147373 A1 | 10/2002 | Dahl et al. |
| 2002/0177743 A1 | 11/2002 | Dahl et al. |
| 2002/0188163 A1 | 12/2002 | Dahl et al. |
| 2002/0193648 A1 | 12/2002 | Dahl et al. |
| 2003/0097032 A1 | 5/2003 | Dahl et al. |
| 2003/0100808 A1 | 5/2003 | Dahl et al. |

FOREIGN PATENT DOCUMENTS

| | | |
|---|---|---|
| FR | 1547516 | 11/1968 |
| WO | 00/14811 A1 | 7/2000 |
| WO | 00/41810 A1 | 7/2000 |
| WO | 00/42124 A1 | 7/2000 |
| WO | 00/42125 A1 | 7/2000 |
| WO | 00/42126 A1 | 7/2000 |
| WO | 00/42127 A1 | 7/2000 |
| WO | 00/42128 A1 | 7/2000 |
| WO | 01/45071 A2 | 6/2001 |

OTHER PUBLICATIONS

International Search Report from PCT/US03/22527 mailed Dec. 2, 2003.
Fort, Jr., et al., *Adamantane: Consequences of the Diamondoid Structure*, Chem. Rev 64, 277-300 (1964).
Sandia National Laboratories (2000), *World's First Diamond Micromachines Created at Sandia*, Press Release, (Feb. 22, 2000) www.Sandia.gov.
Lin, et al., *Natural Occurrence of Tetramantane ($C_{22}H_{28}$), Pentamantane ($C_{26}H_{32}$) and Hexamantane ($C_{30}H_{36}$) in a Deep Petroleum Reservoir*, Fuel 74, (10):1512-1521 (1995).
Dahl, et al., *Diamondoid Hydrocarbons as Indicators of Natural Oil Cracking*, Nature, 54-57 (1999).

(Continued)

*Primary Examiner*—Elizabeth D. Wood
(74) *Attorney, Agent, or Firm*—Buchanan Ingersoll & Rooney PC

(57) ABSTRACT

Hydroprocessing such as hydrocracking is advantageously employed in processes for the recovery and purification of higher diamondoids from petroleum feedstocks. Hydrocracking and other hydroprocesses degrade nondiamondoid contaminants.

31 Claims, 10 Drawing Sheets

OTHER PUBLICATIONS

McKervey, *Synthetic Approaches to Large Diamondoid Hydrocarbons, Tetrahedron 36*, 971-992 (1980).

Chung et al., *Recent Development in High-Energy Density Liquid Fuels, Energy and Fuels 13*, 641-649 (1999).

Balaban et al., *Systematic Classification and Nomenclature of Diamond Hydrocarbons-I, Tetrahedron 34*, 3599-3606 (1978).

Rollman et al, *Adamantane for Petroleum with Zeolites, Abstracts, 210th ACS National Meeting*, Chicago, IL, Aug. 20-24, 1995—Fuel, pp. 1012-1017.

Wingert, *G.C.-M.S. Analysis of Diamondoid Hydrocarbons in Smackover Petroleums, Fuel 71*, 38 (Jan. 1992).

U.S. Appl. No. 10/012,545 "Compositions Comprising Tetramantanes and Processes for Their Separation", filed Dec. 12, 2001, Inventors Dahl, et al.

Beck, J.S., et al., "A New Family of Mesoporous Molecular Sieves Prepared with Liquid Crystal Templates", *J. Am. Chem. Soc.* 114:10834-10843 (1992), no month.

Inoue, Yoshimasa, et al, "Improved Ni-Mo HDN Catalysts through Increased Dispersion and Intrinsic Activity of the Active Phase", *Science and Technology in Catalysis*, Kodansha Ltd., Tokyo, Japan, pp. 415-418 (1998), no month.

*Handbook of Petroleum Refining Processes, Second Edition*, Robert A. Myers, Editor, McGraw Hill (1997) 7.1 "*MAK Moderate—Pressure Hydrocracking*" by M.C. Hunter, et al, no month.

*Handbook of Petroleum Refining Processes, Second Edition*, Robert A. Myers, Editor, McGraw Hill (1997) 7.2 "*Chevron Isocracking—Hydrocracking for Superior Fuel and Lubes Production*" by Alan C. Bridge, no month.

*Handbook of Petroleum Refining Processes, Second Edition*, Robert A. Myers, Editor, McGraw Hill (1997) 7.3 "*UOP Unicracking Process for Hydrocracking*" by Mark Reno, no month.

*Handbook of Petroleum Refining Proceeses, Second Edition*, Robert A. Myers, Editor, McGraw Hill (1997) 8.1 "*Chevron RDS/VRDS Hydrotreating*" by David N. Brossard, no month.

*Handbook of Petroleum Refining Processes, Second Edition*, Robert A. Myers, Editor, McGraw Hill (1997) 8.4 "*UOP RCD Unionfining Process*" by Gregory J. Thompson, no month.

Kresge, et al., *Nature 359*:710 (1992), no month.

GCMS Time (min.) →

FEED  PRODUCT

GCMS Time (min.) ⟶

PROCESSES FOR CONCENTRATING HIGHER DIAMONDOIDS

This application claims priority under 35 U.S.C. § 119 to U.S. Provisional Application No. 60/396,991 entitled Processes for Concentrating Higher Diamondoids and filed on Jul. 18, 2002, the entire content of which is hereby incorporated by reference.

BACKGROUND OF THE INVENTION

1. Field of the Invention

This invention is directed to processes for the concentration, recovery and at least partial purification of higher diamondoid components from petroleum feedstocks.

2. Background Information

The following publications and patents are provided as background and if cited herein may be identified by their superscript numbers:

[1] Fort, Jr., et al., *Adamantane: Consequences of the Diamondoid Structure*, Chem. Rev 64, 277–300 (1964)
[2] Sandia National Laboratories (2000), *World's First Diamond Micromachines Created at Sandia*, Press Release, (2/22/2000) www.Sandia.gov.
[3] Lin, et al., *Natural Occurrence of Tetramantane ($C_{22}H_{28}$), Pentamantane ($C_{26}H_{32}$) and Hexamantane ($C_{30}H_{36}$) in a Deep Petroleum Reservoir*, Fuel 74, (10):1512–1521 (1995)
[4] Dahl, et al., *Diamondoid Hydrocarbons as Indicators of Natural Oil Cracking*, Nature, 54–57 (1999)
[5] McKervey, *Synthetic Approaches to Large Diamondoid Hydrocarbons*, Tetrahedron 36, 971–992 (1980)
[6] Chung et al., *Recent Development in High-Energy Density Liquid Fuels*, Energy and Fuels 13, 641–649 (1999)
[7] Balaban et al., *Systematic Classification and Nomenclature of Diamond Hydrocarbons-I*, Tetrahedron 34, 3599–3606 (1978)
[8] *Handbook of Petroleum Refining Processes*, Second Edition, Robert A. Myers, Editor, McGraw Hill (1997)
   Chapters: 7.1 *"MAK Moderate—Pressure Hydrocracking"* by M. C. Hunter, et al.
   7.2 *"Chevron Isocracking—Hydrocracking for Superior Fuel and Lubes Production"* by Alan C. Bridge
   7.3 *"UOP Unicracking Process for Hydrocracking"* by Mark Reno
   8.1 *"Chevron RDS/VRDS Hydrotreating"* by David N. Brossard, and
   8.4 *"UOP RCD Unionfining Process"* by Gregory J. Thompson
[9] Rollman et al, *Adamantane for Petroleum with Zeolites*, Abstracts, 210th ACS National Meeting, Chicago, Ill., Aug. 20–24, 1995—Fuel, pgs. 1012–1017
[10] Petrov et al., *Saturated Tricyclic C11-C13 Hydrocarbons From (two Soviet) Crude Oils*, Neftekhimiya 13 N3, 345–351 (May-June 1973)
[11] Wingert, G. C.—*M.S. Analysis of Diamondoid Hydrocarbons in Smackover Petroleums*, Fuel 71, 38 (January 1992)
[12] J. Am. Chem. Soc. 114:10834–10843 (1992)
[13] Kresge, et al., Nature 359:710 (1992)
[14] U.S. Pat. No. 3,852,207
[15] U.S. Pat. No. 4,347,121
[16] U.S. Pat. No. 4,401,556
[17] U.S. Pat. No. 4,534,852
[18] U.S. Pat. No. 4,556,646
[19] U.S. Pat. No. 4,820,402
[20] U.S. Pat. No. 4,913,799
[21] U.S. Pat. No. 4,956,747
[22] U.S. Pat. No. 4,956,748
[23] U.S. Pat. No. 4,956,749
[24] U.S. Pat. No. 4,982,049
[25] U.S. Pat. No. 5,019,665
[26] U.S. Pat. No. 5,059,567
[27] U.S. Pat. No. 5,073,530
[28] U.S. Pat. No. 5,080,776
[29] U.S. Pat. No. 5,114,563
[30] U.S. Pat. No. 5,198,203
[31] U.S. Pat. No. 5,246,689
[32] U.S. Pat. No. 5,306,851
[33] U.S. Pat. No. 5,334,368
[34] U.S. Pat. No. 5,414,189
[35] U.S. Pat. No. 5,439,860
[36] U.S. Pat. No. 5,468,372
[37] U.S. Pat. No. 5,498,812
[38] U.S. Pat. No. 5,925,235
[39] U.S. Pat. No. 6,013,239
[40] U.S. Pat. No. 6,179,995
[41] "Improved Ni—Mo HDN catalysts through increased dispersion and intrinsic activity of the active phase" Inoue, Yoshimasa; Uragami, Yuji; Takahashi, Yasuhito; Eijsbouts, Sonja. Nippon Ketjen Co., Ltd., Tokyo, Japan. Studies in Surface Science and Catalysis (1999), 121 Science and Technology in Catalysis (1998)

All of the above publications and patents are herein incorporated by reference in their entirety to the same extent as if each individual publication or patent was specifically and individually indicated to be incorporated by reference in its entirety.

Diamondoids are cage-shaped hydrocarbon molecules possessing amazingly rigid structures that are superimposable fragments of the diamond crystal lattice. Adamantane, a ten-carbon molecule, is the smallest member of the diamondoid series, consisting of one diamond crystal subunit. Diamantane contains two face-fused diamond subuits and triamantane three. Adamantane and diamantane and to a lesser extent, triamantane, are well studied. They have been isolated from petroleum feedstocks and synthesized heretofore. The art has come to refer to adamantane, diamantane, triamantane and substituted analogs thereof as "lower diamondoids". Tetramantane and larger diamondoids and substituted analogs, which exists as multiple isomers are referred as "higher diamondoids". That nomenclature is used herein.

Until recently, the higher diamondoids were only minimally described. Lin, et al.[3] reported the natural occurrence of tetramantane, pentamantane and hexamantane in deep petroleum reservoirs. However, these workers were only able to tentatively identify such compounds in ionized form as part of mass spectroscopy analyses.

Partridge, et al.[25] disclosed a process for concentrating diamondoid-containing hydrocarbon solvents. This process involved three steps. The first was providing a solvent mixture made up of at least 50% by weight normal or slightly-branched $C_5$–$C_{30}$ paraffins having dissolved therein at least one diamondoid compound. In the second step, this mixture is contacted with a shape-selected catalyst in the presence of added hydrogen to convert at least a portion of the normal or slightly branched paraffins to lower-boiling aliplaties and to prevent the conversion of more than about 10% by weight of the diamondoid compounds. In the third step the lower-boiling aliplaties and the diamondoids are separated from one another.

Chen, et al.[34] disclosed methods for isolating high purity lower diamondoid fractions and components. The disclosed methods involved distilling a diamondoid-containing feedstock into five overhead components. These overhead components included adamantane, diamantane and triamantane. Chen, et al. further recited that the pot material recovered after the distillation contained a major amount of substituted triamantane and minor amounts of tetramantane and pentamantane. Again, the Chen et al. identifications were speculative, with no isolations or definitive characterizations.

More recently, present co-inventors Dahl and Carlson filed a series of United States patent applications in which they described the isolation, identification and characterization of a large number of individual higher diamondoids ranging from all four possible tetramantanes through undecamantane.

See for example:
[42] U.S. Ser. No. 10/012,333, now U.S. Pat. No. 6,843,851, issued Jan. 18, 1005;
[43] U.S. Ser. No. 10/012,334, now U.S. Pat. No. 6,828,469, issued Dec. 7, 2004;
[44] U.S. Ser. No. 10/012,335, now U.S. Pat. No. 7,094,937, issued Aug. 22, 2006;
[45] U.S. Ser. No. 10/012,336, now U.S. Pat. No. 6,743,290, issued Jun. 1, 2004;
[46] U.S. Ser. No. 10/012,337, now U.S. Pat. No. 7,034,194, issued Apr. 25, 2006;
[47] U.S. Ser. No. 10/012,545, now U.S. Pat. No. 6,815,569, issued Nov. 9, 2004;
[48] U.S. Ser. No. 10/012,546, now U.S. Pat. No. 6,831,202, issued Dec. 14, 2004;
[49] U.S. Ser. No. 10/012,704, now U.S. Pat. No. 6,812,370, issued Nov. 2, 2004;
[50] U.S. Ser. No. 10/012,709, now U.S. Pat. No. 6,812,371, issued Nov. 2, 2004; and
[51] U.S. Ser. No. 10/017,821, now U.S. Pat. No. 6,844,477, issued Jan. 18, 2005; all filed on Dec. 12, 2001; and
[52] U.S. Ser. No. 10/046,486, filed Jan. 16, 2002, now U.S. Pat. No. 6,858,700, issued Feb. 22, 2005; and
[53] U.S. Ser. No. 10/052,636 filed on Jan. 17, 2002, now U.S. Pat. No. 6,861,569, issued Mar. 1, 2005, and all incorporated herein by reference. These patent applications describe how the higher diamondoids were isolated from petroleum feedstocks such as deep reservoired oils and gas condensates. The concentrations of higher diamondoids in these feedstocks were reported to be quite low, generally in the parts per thousand to parts per billion range. In addition, the relative concentrations of the various higher diamondoids were found to decrease rapidly as the size of the diamondoids increased. The other components of the feedstocks included nondiamondoids including nondiamondoid hydrocarbons, sulfur-containing materials and metal-containing materials and lower diamondoids.

A variety of methods to concentrate and isolate the higher diamondoids were taught in the Dahl and Carlson patent filings. Fractionation procedures, both atmospheric and vacuum, were disclosed and isolated fractions enriched in one or more of the desired higher diamondoids relative to the distillation feedstock were described. Thermal treatment ("pyrolysis") was taught as a desirable process step. In this step the feedstock or a feedstock distillation fraction was heated in a Parr reactor at about 400–500° C. for up to about 20 hours. This pyrolysis step preferentially broke down the nondiamondoid materials to lower molecular weight materials such as gases which were easily removed. The diamondoids, being more stable, were pyrolyzed to a lesser extent. This increased the concentration of the higher diamondoids in the pyrolysis product.

While the pyrolysis step has proven advantageous in its breaking down of nondiamondoid materials, typically it is time consuming and often appears to reduce ultimate yields of the desired higher diamondoids. Accordingly, there is a need for an improved process to assist in the concentration and isolation and recovery of the higher diamondoids.

As will be discussed below, the present invention employs hydroprocessing to treat higher-diamondoid-containing feedstocks and thus to facilitate the separation of higher diamondoids from nondiamondoids. Hydroprocessing is used in many petroleum processing settings. It involves contacting a petroleum feedstock with hydrogen at elevated temperatures, most often with a solid phase catalyst. Subcategories of hydroprocessing include "hydrotreating" and "hydrocracking". "Hydrotreating" is a hydroprocess carried out under conditions to react or remove contaminants from the feedstocks. Such contaminants include sulfur-containing contaminants (in which case the process may be referred to as "hydrodesulfurization"), nitrogen-containing contaminants ("hydrodenitrification"), and metals, which can be in the form of organometallic compounds, ("hydrodemetallation"). Hydrotreating also can include hydrogenation of olefinic and aromatic unsaturation.

In "hydrocracking", petroleum feedstock is contacted with a catalyst at elevated temperatures in the presence of hydrogen to crack or otherwise convert undesired components to more desirable species or to preferentially break down undesired species. The first modern hydrocracking operation was placed on stream in the 1950's by the Standard Oil Company of California. Since the 1960's, hydrocracking has been used in many settings. These include the formation of liquefied petroleum gas (LPG) from naptha feedstocks, the preparation of high quality distillate fuels from gas oils and other heavy stocks, the formation of jet and diesel fuels from vacuum gas oils and the processing of heavy feedstreams such as residuums to fuels and lubricating oils.

In many settings, hydroprocessing involves a combination of several of these reactions taking place simultaneously in the same reaction zone or sequentially in serial zones. As conditions such as temperature, pressure, space velocity and catalysts are altered, the relative impact of the various reactions can change.

SUMMARY OF THE INVENTION

We have now found improved processes for providing compositions enriched in higher diamondoids from petroleum feedstocks or fractions thereof which contain recoverable amounts of these higher diamondoids in admixture with nondiamondoids.

We have found that hydroprocessing such admixtures efficiently reacts and breaks down a significant proportion of the nondiamondoids to materials which are easily separated from the higher diamondoids, and also removes undesired substitutions on higher diamondoid-based compounds to provide higher diamondoids free of such substitutions, thus yielding a product significantly enriched in the desired higher diamondoids. In particular, hydroprocessing can be used to break down and hydrogenate nondiamondoid hydrocarbons and desulfurize higher diamondoids containing sulfur functional groups.

In one general aspect, the invention provides a process for concentrating higher diamondoids from petroleum mixtures containing higher diamondoids in admixture with nondiamondoid materials. This process involves treating the petroleum mixture under hydroprocessing conditions to hydrocrack or otherwise break down or convert at least a portion of the nondiamondoid materials to more easily separated materials. This produces a hydrocracked product containing higher diamondoids and modified nondiamondoid materials. The hydrocracked product is then separated into fractions. At least one fraction is concentrated in higher diamondoids. One or more of the fractions concentrated in higher diamondoids is recovered.

The hydroprocess can be carried out on relatively unprocessed petroleum feedstocks. The hydroprocessing can also involve hydrocracking processes carried out on petroleum-based feedstreams that are the result of hydrotreating steps such as, for example, hydrodemetallation, hydrodenitrification and/or hydrodesulfurization and/or the result of fractionation, or other refining processes. The hydrocracking and hydrotreating can be carried out simultaneously, if desired, as well.

Other hydrocarbon processing procedures that provide broken down products can also be employed in place of or in conjunction with hydroprocessing. Such procedures include, for example, fluid catalytic cracking, slurry catalytic cracking, plasma cracking, and the like. Each of these procedures is well known in the art.

In this aspect, the invention provides processes for concentrating higher diamondoids from petroleum mixtures containing desired higher diamondoids, nondiamondoids, lower diamondoids and optionally sulfur-containing materials including diamondoid sulfides and sulfur-linked diamondoid polymers and dimers, nitrogen-containing materials, metal-containing materials and the like. In these processes, the petroleum mixture may be subjected to one or more pretreatment steps including distillation to form distillation fractions containing desired higher diamondoids and having materials boiling above and/or below the desired higher diamondoids. This pretreatment product contains the desired higher diamondoids in admixture with nondiamondoids and is subjected to hydroprocessing including hydrocracking. The hydroprocessed product contains the desired higher diamondoids and hydrocracked nondiamondoid materials. The product is separated into fractions. At least one fraction is enriched in the desired higher diamondoids. This latter fraction (or fractions) is recovered. This use of hydroprocessing can, in some cases, lead to a simplification or even elimination of some subsequent higher diamondoid isolation and recovery steps.

Other hydroprocessing reactions in addition to hydrocracking can be carried out prior to, simultaneous with or after the hydrocracking. These other processing steps are generally selected from hydrotreating steps and can include hydrodemetallization to remove or convert metal-containing compounds, hydrodesulfurization to break down sulfur-containing compounds including sulfur-linked diamondoid (as especially higher diamondoid)-containing dimers; and hydrodealkylation to remove alkyl substituents from alkyl-substituted higher diamondoids.

The higher diamondoid-containing fractions resulting from the hydroprocessing and subsequent separation may be further processed such as by further distillation, chromatography or like processes to further concentrate and isolate the higher diamondoids they contain.

Overall processes involving one or more hydroprocessing steps in combination with the further processing constitute additional aspects of this invention.

In another aspect, the feedstock may contain higher diamondoid-based compounds such as alkyl higher diamondoids, or higher diamondoids linked together through a sulfur or carrying a sulfur functional group. This may be a naturally-occurring feedstock or a synthetic reaction product. In this aspect, hydroprocessing may be used to convert the higher diamondoid-based compounds to higher diamondoids themselves.

It will also be understood by those skilled in the processing and refining of petroleum feedstocks that some variation of the order of the hydrocracking and some pretreating steps may be desirable. Such variation is within the scope of the present invention.

BRIEF DESCRIPTION OF THE DRAWINGS

This invention will be further described with reference being made to the drawings in which.

DETAILED DESCRIPTION OF THE INVENTION

This invention is directed to the application of hydroprocessing generally (and especially hydrocracking) to processes for the recovery and purification of higher diamondoids from petroleum feedstocks.

This detailed description of the invention is organized as follows.

Feedstocks representative feedstocks for the process are described.

Hydroprocessing Flow Schemes and Conditions—three hydroprocessing process flow schemes are described together with conditions—representative conditions favoring hydrocracking and various hydrotreating reactions.

Catalysts—suitable catalysts are described.

Overall Process Schemes—representative overall process schemes for recovering higher diamondoids incorporating hydroprocessing are described.

This is followed by a series of Examples.

Feedstocks

The terms "feedstock", "hydrocarbonaceous feedstock" and "petroleum feedstock" all refer to hydrocarbonaceous materials comprising recoverable amounts of higher diamondoils. Preferably, such feedstocks include oil, gas condensates, refinery streams, oils derived from reservoir rocks, oil shale, tar sands, and source rocks, and the like. Feedstocks often contain significant quantities of sulfur most commonly as organic sulfur compounds. Sulfur-linked dimers and even trimers of diamondoids including higher diamondoids are often present in feedstocks. Feedstocks typically include one or more lower diamondoids as well as nondiamondoid components. The latter are typically characterized as comprising nondiamondoid-structure organic compounds having boiling points within the range of boiling points of the higher diamondoids. Aromatics can be significant nondiamondoid materials whose removal can be particularly advantageous. Typical feedstocks may also contain impurities such as sediment, metals including nickel and, vanadium and other inorganics. They may also include nondiamondoid-heteromolecules containing sulfur, nitrogen and the like. All of these nondiamondoid materials are included in "nondiamondoid components" as that term is used herein. As will be described below, a feedstock may be fractionated; demetallized, denitrified and/or desulfurized such as by hydrotreating; and/or otherwise treated prior to being hydrocracked or otherwise hydroprocessed.

Figure 3:
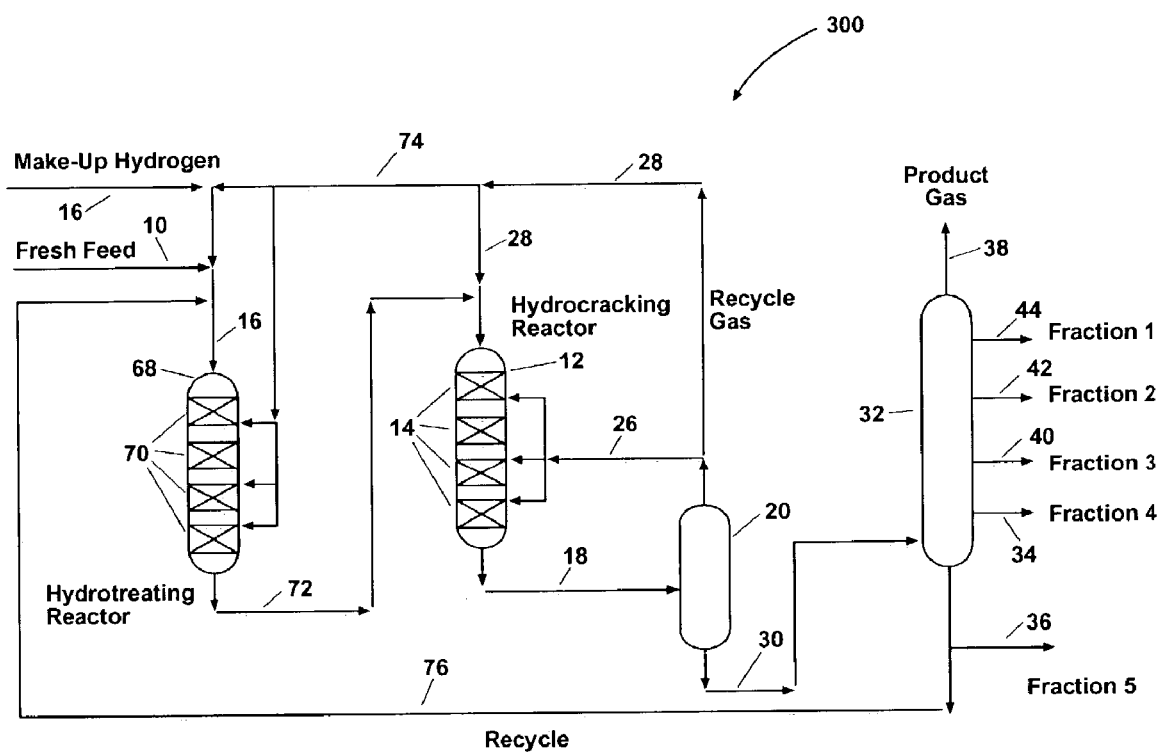
FIG. 3 is a schematic illustration of the process flow in a representative recycle hydrotreating and hydrocracking process of this invention.

Suitable feedstocks may also include recycled materials containing recoverable amounts of higher diamondoids. An example of a process providing such a recycle-containing feedstock is illustrated in FIG. 3. Feedstocks can include materials containing higher diamondoid and obtained from incomplete or undesired reactions of higher diamondoids to form functionalized higher diamondoids. In the latter case, compositions containing materials having undesired functionalization, for example, thiol, amino, nitro and similar functionalization of diamondoids, may be desirably used as feedstocks wherein the subsequent hydroprocesses conveniently remove such functionality thereby regenerating the higher diamondoid free of such substitution.

The term "diamondoid" refers to substituted and unsubstituted caged compounds of the adamantane series including substituted and unsubstituted adamantane, diamantane, triamantane, tetramantane, pentamantane, hexamantane, heptamantane, octamantane, nonamantane, decamantane, undecamantane, and the like and also including various molecular weight forms of these components and including isomers of these forms. Substituted diamondoids preferably comprise from 1 to 10 and more preferably 1 to 4 alkyl substituents. "Diamondoids" include "lower diamondoids" and "higher diamondoids".

The term "lower diamondoids" or "adamantane, diamantane and triamantace" refers to any and/or all unsubstituted and substituted derivatives of adamantane, diamantane and triamantane. The unsubstituted lower diamondoids show no isomers and are readily synthesized, distinguishing them from the "higher diamondoids".

The term "higher diamondoids" refers to any and/or all substituted and unsubstituted tetramantanes; to any and/or all substituted and unsubstituted pentamantanes; to any and/or all substituted and unsubstituted hexamantanes; to any and/or all substituted and unsubstituted heptamantanes; to any and/or all substituted and unsubstituted octamantanes; to any and/or all substituted and unsubstituted nonamantanes; to any and/or all substituted and unsubstituted decamantanes; to any and/or all substituted and unsubstituted undecamantanes; as well as mixtures of the above as well as isomers and stereoisomers.

In the processes of this invention, a feedstock is selected that contains recoverable amounts of one or more selected higher diamondoids. Preferably, such feedstock comprises at least about 1 ppb of one or more higher diamondoids, more preferably, at least about 25 ppb and still more preferably at least about 100 ppb. It is understood, of course, that feedstocks having higher concentrations of higher diamondoids facilitate recovery of these components.

Preferred feedstocks include, for example, natural gas condensates and refinery streams having high concentrations of higher diamondoids. With regard to the latter, such refinery streams include hydrocarbonaceous streams recoverable from cracking processes, distillations, coking and the like. Particularly preferred feedstocks include gas condensate feedstocks recovered from the Norphlet Formation in the Gulf of Mexico and from the LeDuc Formation in Canada.

In one embodiment, the feedstocks used in the processes of this invention typically comprise nondiamondoid components and diamondoid dimers, such as lower diamondoid dimers having a sulfide linkage, all having boiling points within the range of the higher diamondoids selected for recovery as well as one or more lower diamondoid components. These feedstocks will usually contain a mixture of higher diamondoids.

In such feedstocks, higher diamondoid components often cannot be effectively recovered directly from the feedstock because of their low concentrations. Accordingly, the processes of this invention may entail pretreatment steps to remove a sufficient amount of nondiamondoids and lower diamondoids from the feedstock under conditions to provide a treated feedstock from which the selected higher diamondoid components can be recovered.

In one embodiment, the removal of these materials includes a first distillation of the feedstock to remove nondiamondoid components as well as lower diamondoid components as overhead and leave a higher diamondoid-enriched first bottoms.

A second distillation can be operated to fractionate the first bottoms and provide several cuts in a temperature range of interest enriched in the selected higher diamondoids or groups of selected higher diamondoids. The cuts, which are enriched in one or more selected higher diamondoids or a particular higher diamondoid of interest, are retained and typically require further purification such as by the hydroprocesses of the present invention. The following Table 1 illustrates representative fractionation points (atmospheric equivalent boiling points) that may be used to enrich various higher diamondoids in overheads. In practice it may be advantageous to make wider temperature range cuts which would often contain groups of higher diamondoids which could be separated in subsequent separation steps.

TABLE 1

Fractionation Points

| Higher Diamondoid | Most Preferred | | Preferred | |
|---|---|---|---|---|
| | Lower Cut Temperature (° C.) | Higher Cut Temperature (° C.) | Lower Cut Temperature (° C.) | Higher Cut Temperature (° C.) |
| Tetramantanes | 349 | 382 | 330 | 400 |
| Pentamantanes | 385 | 427 | 360 | 450 |
| Cyclohexamantanes | 393 | 466 | 365 | 500 |
| Hexamantanes | 393 | 466 | 365 | 500 |
| Heptamantanes | 432 | 504 | 395 | 540 |
| Octamantanes | 454 | 527 | 420 | 560 |
| Nonamantanes | 463 | 549 | 425 | 590 |
| Decamantanes | 472 | 571 | 435 | 610 |
| Undecamantanes | 499 | 588 | 455 | 625 |

| Higher Diamondoid | Useful | |
|---|---|---|
| | Lower Cut Temperature (° C.) | Higher Cut Temperature (° C.) |
| Tetramantanes | 300 | 430 |
| Pentamantanes | 330 | 490 |
| Cyclohexamantanes | 330 | 550 |
| Hexamantanes | 330 | 550 |
| Heptamantanes | 350 | 600 |
| Octamantanes | 375 | 610 |
| Nonamantanes | 380 | 650 |
| Decamantanes | 390 | 660 |
| Undecamantanes | 400 | 675 |

Other pretreatment processes for the removal of lower diamondoids, and/or hydrocarbonaceous nondiamondoid components include, by way of example only, size separation techniques, evaporation either under normal or reduced pressure, crystallization, chromatography, well head separators, reduced pressure and the like. For example, lower diamondoids can be preferentially removed from feedstocks using a variety of techniques such as are described in commonly-owned copending patent application U.S. Ser. No. 10/017,821[52]. Adamantane and diamantane dissolved in deep gases may crystallize during commercial gas and petroleum liquid production due to a drop in pressure. Commercially-available well head separators effectively remove lower diamondoids from such feedstocks to avoid scaling problems in oil and gas production equipment. Other removal processes can utilize the larger sizes of the higher diamondoids to effect separation of lower diamondoids therefrom. For example, size separation techniques using membranes will allow a feedstock retained in the membrane to selectively pass lower diamondoids across the membrane barrier provided that the pore size of the membrane barrier is selected to differentiate between compounds having the size of higher diamondoid components as compared to lower diamondoid components. The pore size of molecular sieves such as zeolites and the like can also be used to effect size separations.

Hydroprocessing Flow Schemes and Conditions

In hydroprocessing a feedstream is contacted with hydrogen at an elevated temperature most commonly in the presence of a suitable base metal or noble metal containing catalyst to bring about hydrocracking and/or hydrotreating (including hydrogenation of unsaturation, hydrodemetallization, hydrodesulfurization and/or hydrodenitrification). While these various conversion steps have been accorded separate names, it will be appreciated that, depending upon the materials present in the feedstock and the reaction conditions imposed, a single treatment in a single reaction zone can result in combinations of these reactions taking place simultaneously or sequentially.

The severity of the hydroprocessing conditions is adjusted depending on the feedstock and the process objectives. In general, more strenuous conditions provide higher degrees of cracking of nondiamondoid but also may lead to some breaking down of desired higher diamondoids, as well. Hydrocracking reduces the size of the nondiamodoid hydrocarbon molecules and often is accompanied by same hydrogenation of olefinic and aromatic unsaturation. Desulfurization and denitrification of the feedstock will also usually occur to some extent. The hydroprocessed product is then separated into various boiling range fractions. The separation is typically conducted by fractional distillation preceded by one or more vapor-liquid separators to remove hydrogen and/or other gases.

Generally, in hydrotreating operations, cracking of the hydrocarbon molecules is less pronounced and the unsaturated hydrocarbons are either fully or partially hydrogenated. This generally calls for conditions, somewhat less severe than those used for cracking. In all cases, however, the conditions are selected with consideration for optimizing the recovery and yield of desired higher diamondoids.

Hydroprocessing conditions useful in this invention include temperatures in the range of from about 300 to about 950° F. (150 to 510° C.) arid preferably 400 to 925° F. (204 to 495° C.). In the experiments shown in the examples, base metal containing catalysts gave best results at temperatures in the range of 600–875° F. and especially 675–850° F. and noble metal catalysts gave best results at temperatures in the range of 625–925° F. and especially 700–925° F.

Total pressure (added hydrogen plus feedstock pressure) is in the range of 200 to 4000 psi and preferably 500 to 3500 psi and especially 900 to 3000 psi.

Hydrocarbon feed rates expressed as reactor space velocities (or liquid hourly space velocities "LHSV's") of about 0.02 to 20 hrs$^{-1}$, preferably 0.04 to 5 hrs$^{-1}$ and especially 0.05 to 4 hrs$^{-1}$ are employed.

Hydrogen circulation rates ($H_2$/liquid ratios) are generally in the range of from about 200 standard cubic feet (scf) per barrel to about 20,000 scf/bbl and preferably 400 to 10,000 scf/bbl.

Figure 1:
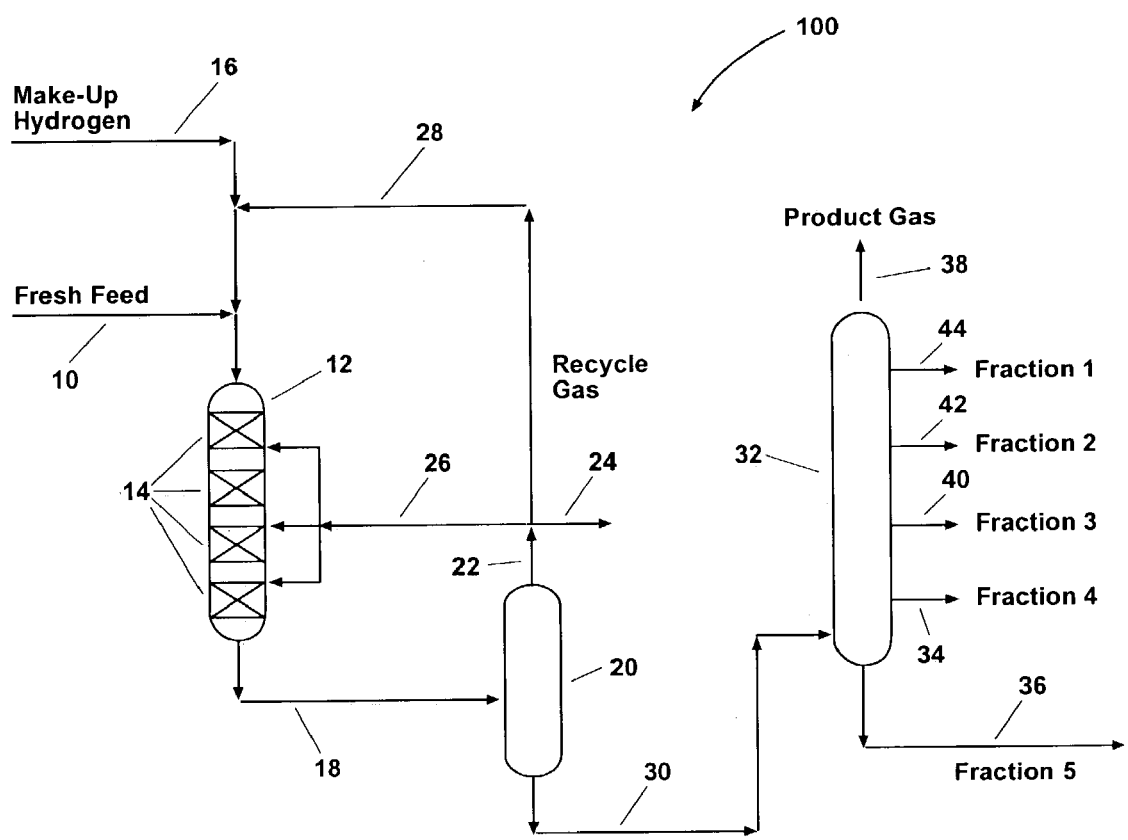
FIG. 1 is a schematic illustration of a representative process flow diagram for a single stage hydroprocess of this invention.

As shown in FIG. 1, hydroprocessing such as hydrocracking is usually carried out as a continuous process in which a higher diamondoid-containing feedstock is passed through line 10 to reactor 12 which contains bed(s) 14 of hydroprocessing (hydrocracking) catalyst. Gaseous hydrogen is fed under pressure to reactor 12 via line 16. Such hydrogen streams originate from, for example, a hydrogen plant or, a reforming reactor, or as hydrogen recycled from hydrocracker effluent. Purity of the gaseous stream will depend on a number of factors, but will generally be greater than 50% hydrogen, and often greater than about 90% hydrogen or higher. The reactor temperature, pressure and space velocity are all controlled to provide conditions under which nondiamondoid components of the feedstock are broken down or modified. The hydrockate is removed from reactor 12 via line 18 typically to a liquid/gas separator 20 where a gas stream containing unreacted hydrogen and gaseous breakdown products such as hydrogen sulfide and gaseous alkanes and the like is taken off overhead via line 22 either to vent or recovery via line 24 or to recycle via lines 26 and/or 28. Preferably, hydrocracking is continued for a sufficient period and at a sufficiently high temperature to crack, hydrogenate or otherwise convert at least about 10% of the nondiamondoid components (more preferably at least about 50% and even more preferably at least about 75%) from the hydrocracker feedstock based on the total weight of the nondiamondoid components in the feedstock prior to hydrocracking. A liquid phase product made up of higher diamondoids and liquid cracked nondiamondoids as well as other materials is taken off as a bottoms via line 30 to a fractionator 32 where it is split into two or more fractions—some of Which are rich in higher diamondoids (typically the higher boiling fractions such as represented by fractions 4 and 5 removed via lines 34 and 36) and some of which are rich in nondiamondoid cracking products (typically a gas fraction represented by line 38 and lower boiling liquid fractions represented by lines 40, 42 and 44). Fractionator 32 is most commonly one or more distillation columns. It would also be understood to those versed in the art that the various process steps could also be run in a batch mode with intermediate storage.

Figure 2:
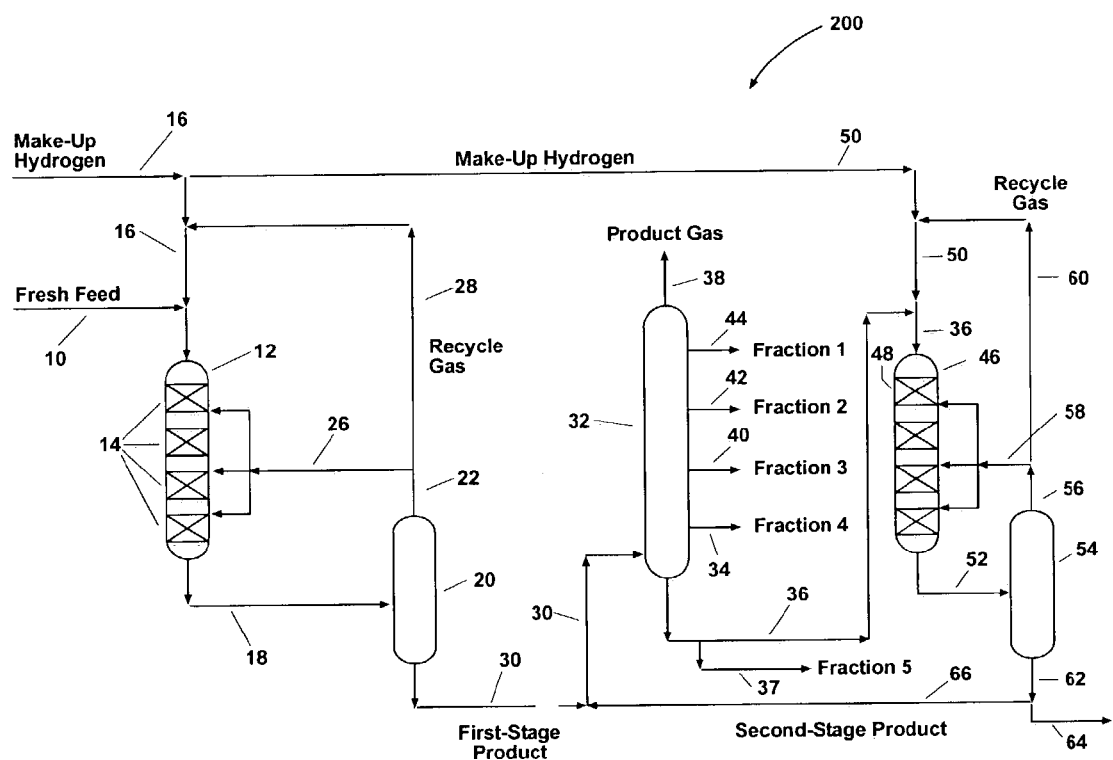
FIG. 2 is a schematic illustration of the process flow in a representative two stage hydroprocess of this invention.

Hydroprocessing (hydrocracking) can also be carried out in two or more stages. FIG. 2 shows a representative multi-stage hydrocracker. The first stage is similar to the single stage unit depicted in FIG. 1. In the process shown in FIG. 2, the bottoms fraction from fractionator 32 is taken off via line 36 and if desired a portion of it can be removed via line 37. The remainder of the higher diamondoid-rich bottoms fraction is fed to second hydrocracking reactor 46 which contains bed(s) 48 of hydrocracking catalyst which may be the same or different than the catalyst used in the first stage. Similarly, the reaction conditions may be the same as or varied from those present in the first stage. Hydrogen is added via line 50 and a second stage hydrockate is removed via line 52 to separator 54 where a second gas phase made up of hydrogen and gaseous cracking products is taken off via line 56 and recycled to hydrocracker 46 via lines 58 and/or 60. The liquid phase fraction of the hydrockate is removed via line 62. A portion of this stream is removed as product, line 64, and the remainder is recycled to fractionator 32 via line 66 so that light products can be removed and the higher diamondoids can be concentrated in high boiling fractions such as fractions 4 or 5. The product from line 64 is also concentrated in higher diamondoids.

If desired, multiple hydroprocessing zones operated at varied conditions to favor multiple cracking and treating reactions may be used to facilitate the recovery of higher diamondoids in accord with this invention. FIG. 3 depicts a processing scheme in which hydroprocessing under conditions favoring hydrotreating and hydroprocessing under conditions favoring hydrocracking are carried out sequentially with liquid recycle. In addition and as noted above, other hydrocarbon processing procedures that provide cracked products can also be employed in place of or in conjunction with hydrocracking. Such procedures include, for example, coking, catalytic cracking, fluid catalytic cracking, slurry catalytic cracking, and the like.

Specifically, in FIG. 3, higher diamondoid-containing feed is fed via line to hydrotreating reactor 68 which contains hydrotreating catalyst 70. Hydrogen is fed via line 16 to reactor 68. The catalyst and reaction conditions in reactor 68 are chosen to treat the feed and remove or react one or more contaminants such as metals (hydrodemetallization), sulfur (hydrodesulfurization), or nitrogen-containing materials (hydrodenitrification). Hydrotreated product is removed via line 72 and charged as feed to hydrocracking reactor 12. The hydrocracking proceeds as described in FIG. 1 with the following changes. Generally the hydrogen required for hydrocracking in reactor 12 is provided at least in part as recycle gas from separator 20 via line 28. Recycle gas containing hydrogen can also be recycled to reactor 68 via line 74. Also, the bottoms fraction taken off of fractionator 32, which generally is rich in higher diamondoids, may be removed as product via line 36 but more commonly is in part recycled to hydrotreating reactor 68 via line 76.

These three hydroprocessing flow schemes are representative. Although processes providing at least a degree of hydrocracking have proven very helpful, one could employ hydrotreating alone. Also, one could separate the hydrocracking and hydrotreating stage in the overall process scheme. The number of reactors and fractionators and their locations in the process scheme can also be varied.

Hydroprocessing Catalysts

Catalysts used in carrying out hydroprocessing operations are well known in the art. See for example U.S. Pat. Nos. 5,925,235[38], 5,439,860[35], 3,852,207[14], and 4,347,121[15], for general descriptions of hydrotreating, hydrocracking, and typical catalysts used in such processes.

Suitable catalysts include noble metals from Group VIII, such as platinum, gold or palladium on an alumina or siliceous matrix. Another group of catalysts have Group VIII and Group VIB nonnoble or base metals, such as nickel, cobalt, molybdenum, and tungsten on an alumina or siliceous matrix. More than one base metal may be used. For example, combinations of nickel-molybdenum, nickel-tungsten, or cobalt-molybdenum can be used. Nickel-tin can also be used. U.S. Pat. No. 5,468,372[36] describes a very suitable base metal (Ni/Mo) catalyst. U.S. Pat. No. 4,556,646[18] describes a noble metal catalyst. Other suitable catalysts are described, for example, in U.S. Pat. No. 5,925,235[38] and U.S. Pat. No. 5,439,860[35] as well as U.S. Pat. No. 6,534,437[55] and WO's 0041810[56]; 0041811[57]; 0042124[58]; 0042125[59]; 0042126[60], 0042127[61] and 0042128[62]. Excellent results may be achieved with the Akzo-Nobel "Stars" and "Nebula" commercial base metal catalysts. The base metals (such as nickel-molybdenum) are usually present in the final catalyst composition as oxides, or as sulfides.

Preferred non-noble metal catalyst compositions contain in excess of about 5 weight percent, preferably about 5 to about 40 weight percent molybdenum and/or tungsten, and at least about 0.5, and generally about 1 to about 15 weight percent of nickel and/or cobalt determined as the corresponding oxides. The noble metal (such as platinum, gold or palladium) catalysts contain in excess of 0.01 percent noble metal, preferably between 0.1 and 1.0 percent metal. Combinations of noble metals may also be used, such as mixtures of platinum, gold and palladium. Combinations of noble and base metals may also be in the catalysts.

The metal components (or compounds thereof) can be incorporated into the overall catalyst composition by any one of numerous procedures, including co-mulling, impregnation, or ion exchange and other techniques familiar to those versed in the art.

The matrix component can be of many types including some that have acidic catalytic activity. Ones that have activity include amorphous silica-alumina, or a zeolitic or non-zeolitic crystalline molecular sieve. Examples of suitable matrix molecular sieves include zeolite Y, zeolite X and the so called ultra stable zeolite Y and high structural silica:alumina ratio zeolite Y such as those described in U.S. Pat. Nos. 4,401,556[16], 4,820,402[19] and 5,059,567[26]. Small crystal size zeolite Y, such as that described in U.S. Pat. No. 5,073,530[27], can also be used. Non-zeolitic molecular sieves which can be used include, for example, silicoaluminophosphates (SAPO), ferroaluminophosphate, titanium aluminophosphate and the various ELAPO molecular sieves described in U.S. Pat. No. 4,913,799[20] and the references cited therein. Details regarding the preparation of various non-zeolite molecular sieves can be found in U.S. Pat. Nos. 5,114,563[29] (SAPO); 4,913,799[20] and the various references cited-in U.S. Pat. No. 4,913,799[20]. Mesoporous molecular sieves can also be used, for example the M41S family of materials (J. Am. Chem. Soc. 114:10834–10843(1992[12])), MCM-41 (U.S. Pat. Nos. 5,246,689[31]; 5,198,203[30]; 5,334,368[33]), and MCM-48 (Kresge et al., Nature 359:710 (1992[13]))

Suitable matrix materials may also include synthetic or natural substances as well as inorganic materials such as clay, silica and/or metal oxides such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia, and silica-magnesia-zirconia. The latter may be either naturally occurring or in the form of gelatinous precipitates or gels including mixtures of silica and metal oxides. Naturally occurring clays which can be composited with the catalyst include those of the montmorillonite and kaolin families. These clays can be used in the raw state as originally mined or initially subjected to calumniation, acid treatment or chemical modification. Syntheticlays such as are described in U.S. Pat. No. 5,495,283[63] and WO 0146071[64] can also be employed.

A particularly suitable noble metal catalyst comprises a Y-type zeolite, which has a unit cell size of about 24.35 Å, a $SiO_2/Al_2O_3$ ratio greater than 5.0, a surface area greater than 500 $m^2/g$, and a sodium content of about 0.2 wt %. This Y-type zeolite, which is stable in dry air to about 1000° C., may be used in the catalyst base. The ratio by weight of the amorphous inorganic oxide component to the zeolite component in the catalyst base is generally between 1:4 and 4:1, preferably between 1:2 and 2:1. Such a catalyst, made up of 60% wt Y-type zeolite and 40% alumina and carrying 0.5% wt palladium was used in the present Example 1.

Furthermore, more than one catalyst type may be used in the reactor. The different catalyst types can be separated into layers or mixed. For example, hydrotreating catalyst and hydrocracking catalyst can be layered or mixed in a single reactor. Examples of mixed and layered catalyst systems are described in U.S. Pat. Nos. 5,925,235[38] and 5,439,860[35].

U.S. Pat. No. 4,534,852[17] describes a high-activity hydrotreating catalyst system. The upper bed consists of a catalyst containing from about 2–4 wt % nickel from about 8–15 wt % molybdenum and from about 2–4 wt % phosphorus supported on a carrier consisting mostly of alumina. The lower bed consists of a high-activity, hydrodesulfurization catalyst Containing from about 2–4 wt % cobalt and/or nickel, from about 8–15 wt % molybdenum and less than about 0.5 wt % phosphorus supported on a carrier consisting mostly of alumina.

These materials are merely representative of the many hydrocracking and hydrotreating catalysts known in the field of petroleum processing which can be used.

The choice of catalyst may be dictated at least in part by the nature of the feed being processed and the hydroprocessing conversions desired. For example, relatively acidic noble metal catalysts such as those on zeolite clay or amorphorus aluminasilicate substrates can provide efficient cracking of high-boiling contaminants. They also may favor dealkylating alkyl higher diamondoids which may be desirable.

Some feeds contain large amounts (as much as 6–8% w) sulfur often linking diamondoids and higher diamondoids into dimers and the like. These high sulfur levels can deactivate noble metal catalysts. Base metal catalysts are often more stable and retain activity better in the presence of sulfur.

Overall Process Schemes

Hydroprocessing schemes such as those shown in FIGS. 1, 2 and 3 can be incorporated into overall process schemes for concentrating and recovering higher diamondoids. For example, FIG. 4 illustrates hydroprocessing scheme 100 of FIG. 1 incorporated into such an overall process.

Figure 4:
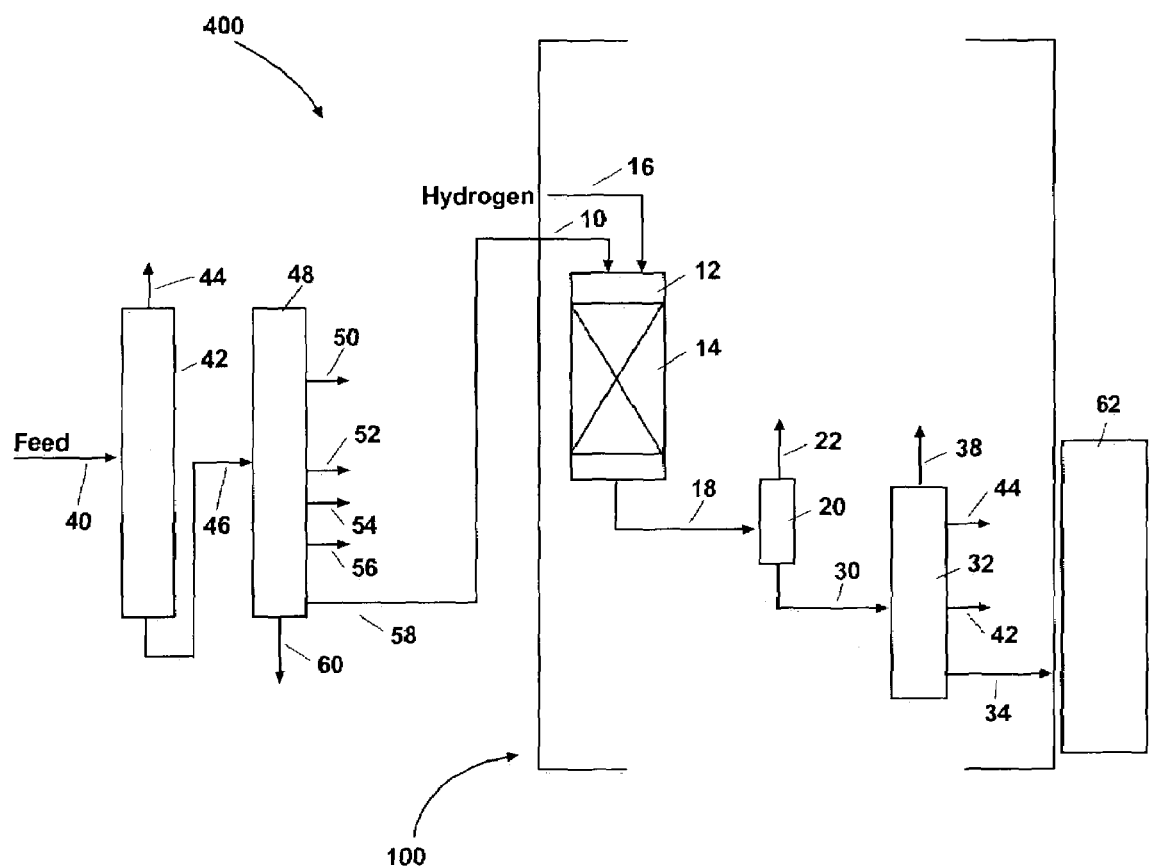
FIG. 4 is a schematic illustration of an overall higher diamondoid recovery process showing the incorporation of the hydroprocessing of this invention.

In FIG. 4, an overall diamondoid recovery process 400 is shown. In this process, scheme 100 is preceded by a pair of distillation columns. It will be appreciated that scheme 100 could be scheme 200 or 300 of FIGS. 2 and 3, as well as other hydroprocessing configurations. Diamondoid-containing feedstock is fed through line 40 to atmospheric distillation column 42 where light components are taken overhead and removed via lines 44, 80 and 82. An atmospheric residuum product containing the higher diamondoids as well as other heavy components is taken off via line 46 to vacuum distillation column 48. In column 48 a variety of cuts are taken represented by distillate lines 50, 52, 54, 56, 58 and bottoms line 60. Typically, the vacuum column can be operated to give several distillate cuts containing higher diamondoids with the higher materials being higher boiling and thus appearing in the higher boiling fractions such as represented by lines 56 and 58 and in residuum represented by line 60. A representative higher-diamondoid containing cut removed via line 58 is used as feed for the hydroprocessing unit, which operates as set forth in FIGS. 1, 2 and 3.

By carrying out these optional distillation steps before hydrocracking, it is possible to separate the diamondoid-containing feed from some metal-containing, sulfur-containing and/or nitrogen containing species which are often present in the crude feedstocks fed through line 40. The materials may poison or deactivate the hydroprocessing catalyst in bed 14. These problems are reduced by the pretreatment distillations.

As further shown in FIG. 4 one or more of the diamondoid-containing fractions taken off of column 32 via lines 34, 42 and/or 44 can be passed to post-processing stage 62. As described in detail in U.S. Ser. No. 10/059,636[5], post-processing stage 62 can employ one or more chromatographic steps, including gas chromatography, high performance liquid chromatography, crystallization, thermal diffusion techniques, zone refining, progressive recrystalization, size separation and the like to isolate and remove individual higher diamondoids. In such a process, the recovered feedstock may be first subjected to gravity column chromatography using silver nitrate impregnated silica gel to remove aromatics. In some cases, aromatic levels are so reduced in the product that this step can be eliminated. This can be followed by HPLC using two different columns of differing selectivities to isolate the target higher diamondoids; and crystallization to provide crystals of pure target higher diamondoids. Where higher diamondoid concentrations are not high enough for crystallization to occur, further concentration by, for example, preparative capillary gas chromatography, may be necessary.

It will be appreciated that various sub-units of the process scheme can be operated in batch mode with intermediate storage.

Compositions and Utility

The above processes provide novel higher diamondoid compositions. For example, in one embodiment, these processes provide a composition comprising at least tetramantane and pentamantane components wherein said composition comprises at least about 10 weight percent tetramantane components and at least about 0.5 weight percent pentamantane components based on the total amount of diamondoid components present. These higher diamondoids are useful for special polymers, in micro- and molecular-electronics and in nanotechnology applications. In particular, the rigidity, strength, stability, thermal conductivity, variety of structural forms and multiple attachment sites shown by these molecules makes possible accurate construction of robust, durable, precision devices with nanometer dimensions.

EXAMPLE 1

This Example shows on overall process and has seven steps.

Step 1. Feedstock selection
Step 2. GCMS assay
Step 3. Feedstock atmospheric distillation
Step 4. Vacuum fractionation of atmospheric distillation residue
Step 5. Hydroprocessing of selected fractions
Step 6. Removal of aromatic and polar nondiamondoid components
Step 7. Multi-column HPLC isolation of higher diamondoids
  a) First column of first selectivity to provide fractions enriched in specific higher diamondoids.
  b) Second column of different selectivity to provide isolated higher diamondoids.

Step 1—Feedstock Selection

Suitable starting materials were obtained. These materials included a gas condensate, Feedstock A, and a gas condensate containing petroleum components, Feedstock B. Although other condensates, petroleums, or refinery cuts and products could have been used, these two materials were chosen due to their high diamondoid concentration, approximately 0.3 weight percent higher diamondoids, as determined by GC and GC/MS. Both feedstocks were light colored and had API gravities between 19 and 20° API.

Step 2—GC/MS Assay

Feedstock A was analyzed using gas chromatography/mass spectrometry to confirm the presence of target higher diamondoids and to provide gas chromatographic retention times for these target materials. This information is used to track individual target higher diamondoids through subsequent isolation procedures.

Step 3—Feedstock Atmospheric Distillation

A sample of Feedstock B was distilled into a number of fractions based on boiling points to separate the lower boiling point components (nondiamondoids and lower diamondoids) and for further concentration and enrichment of particular higher diamondoids in various fractions. The yields of atmospheric distillate fractions of two separate samples of Feedstock B are shown in Table 2, below and are contrasted to simulated distillation yields. As seen from Table 2, the simulated distillation data are in agreement with the actual distillation data. The simulated distillation data were used to plan subsequent distillations.

TABLE 2

Yields of Atmospheric Distillation Fractions from Two Separate Runs of Feedstock B

| Cut (° F.) | Sim Dis Est.'d Yields (Wt %) | Feedstock B (Run 2) Yields (Wt %) | Difference |
| --- | --- | --- | --- |
| To 349 | 8.0 | 7.6 | 0.4 |
| 349 to 491 | 57.0 | 57.7 | −0.7 |
| 491 to 643 | 31.0 | 30.6 | 0.4 |
| 643 and higher | 4.0 | 4.1 | −0.1 |

| Cut (° F.) | Sim Dis Est.'d Yields (Wt %) | Feedstock B (Run 1) Yields (Wt %) | Difference |
| --- | --- | --- | --- |
| To 477 | 63.2 | 59.3 | 3.9 |
| 477 to 515 | 4.8 | 7.3 | −2.5 |
| 515 to 649 | 28.5 | 31.2 | −2.7 |
| 649 and higher | 3.5 | 2.1 | 1.4 |

Step 4—Fractionation of Atmospheric Distillation Residue by Vacuum Distillation

The resulting Feedstock B atmospheric residuum from Step 3 (comprising 2–4 weight percent of the original feedstock) was distilled into fractions containing higher diamondoids). The feed to this high temperature distillation process was the atmospheric 650° F.+bottoms. Table 3 illustrates the distillation reports for Feedstock B 650° F.+distillation bottoms.

TABLE 3

Distillation Report for Feedstock B-btms
Feedstock B - Atmospheric distillation resid 650° F. + bottoms
Column Used: Sarnia HiVac

| CUT | VAPOR TEMP ST - END, ° F. | WEIGHT G | VOLUME ml @ 60° F. | API 60/60 | DENSITY 60° F. | WT PCT | VOL PCT | WT PCT | VOL PCT |
| --- | --- | --- | --- | --- | --- | --- | --- | --- | --- |
| 1 | 601–656 | 666.4 | 639 | 4.1 | 1.0435 | 20.12 | 19.38 | 20.03 | 19.40 |
| 2 | 656–702 | 666.9 | 646 | 5.6 | 1.0321 | 20.14 | 19.59 | 20.05 | 19.62 |
| 3 | 702–752 | 334.3 | 330 | 8.3 | 1.0122 | 10.09 | 10.01 | 10.05 | 10.02 |
| 4 | 752–800 | 167.7 | 173 | 14.5 | 0.9692 | 5.06 | 5.25 | 5.04 | 5.25 |
| 5 | 800–852 | 167.3 | 181 | 21.7 | 0.9236 | 5.05 | 5.49 | 5.03 | 5.50 |
| 6 | 852–900 | 167.1 | 181 | 21.9 | 0.9224 | 5.05 | 5.49 | 5.02 | 5.50 |
| 7 | 900–950 | 238.4 | 257 | 21.2 | 0.9267 | 7.25 | 7.79 | 7.17 | 7.80 |
| 8 | 950–976 | 85.4 | 91 | 18.9 | 0.9408 | 2.58 | 2.76 | 2.57 | 2.76 |
| 9 | 976–1000 | 80.8 | 85 | 18.2 | 0.9452 | 2.44 | 2.58 | 2.43 | 2.58 |

TABLE 3-continued

Distillation Report for Feedstock B-btms
Feedstock B - Atmospheric distillation resid 650° F. + bottoms
Column Used: Sarnia HiVac

| 10 | 1000–1026 | 93.8 | 98 | 16.9 | 0.9535 | 2.83 | 2.97 | 2.82 | 2.98 |
|---|---|---|---|---|---|---|---|---|---|
| COL HOLDUP | | 4.0 | 4 | 3.4 | 1.0489 | 0.12 | 0.12 | 0.12 | 0.12 |
| BTMS | 1026+ | 621.8 | 593 | 3.4 | 1.0489 | 18.78 | 17.98 | 18.69 | 18.01 |
| EOR TRAPS | | 17.8 | 20 | | | 0.54 | 0.61 | 0.54 | 0.61 |
| TOTALS | | 3311.7 | 3298 | | | 100.00 | 100.00 | 99.56 | 100.15 |
| LOSS | | 14.6 | −5 | | | | | 0.44 | −0.15 |
| FEED | | 3326.3 | 3293 | 8.6 | 1.0100 | | | 100.00 | 100.00 |
| BACK CALCULATED API & DENSITY | | | | 9.4 | 1.0039 | | | | |

TABLE 4

Elemental Composition of Feedstock B
Analyses on Feedstock B 650 + F Resid

| Measured | Value |
|---|---|
| Nitrogen | 0.991 wt % |
| Sulfur | 0.863 wt % |
| Nickel | 8.61 ppm |
| Vanadium | <0.2 ppm |

Table 4 illustrates the partial elemental composition of Feedstock B atmospheric distillation (650° F.) residue including some of the identified impurities. Table 4 displays the weight percent nitrogen, sulfur, nickel and vanadium in Feedstock B atmospheric distillation residue. Subsequent steps remove these materials.

Step 5—Hydroprocessing of Isolated Fractions

A feed made by combining materials from distillate cuts 4 and 5 (Table 3B) was prepared and analyzed for diamondoids and nondiamondoids using a gas chromatograph mass spectrometer ("GCMS).

Figure 5:
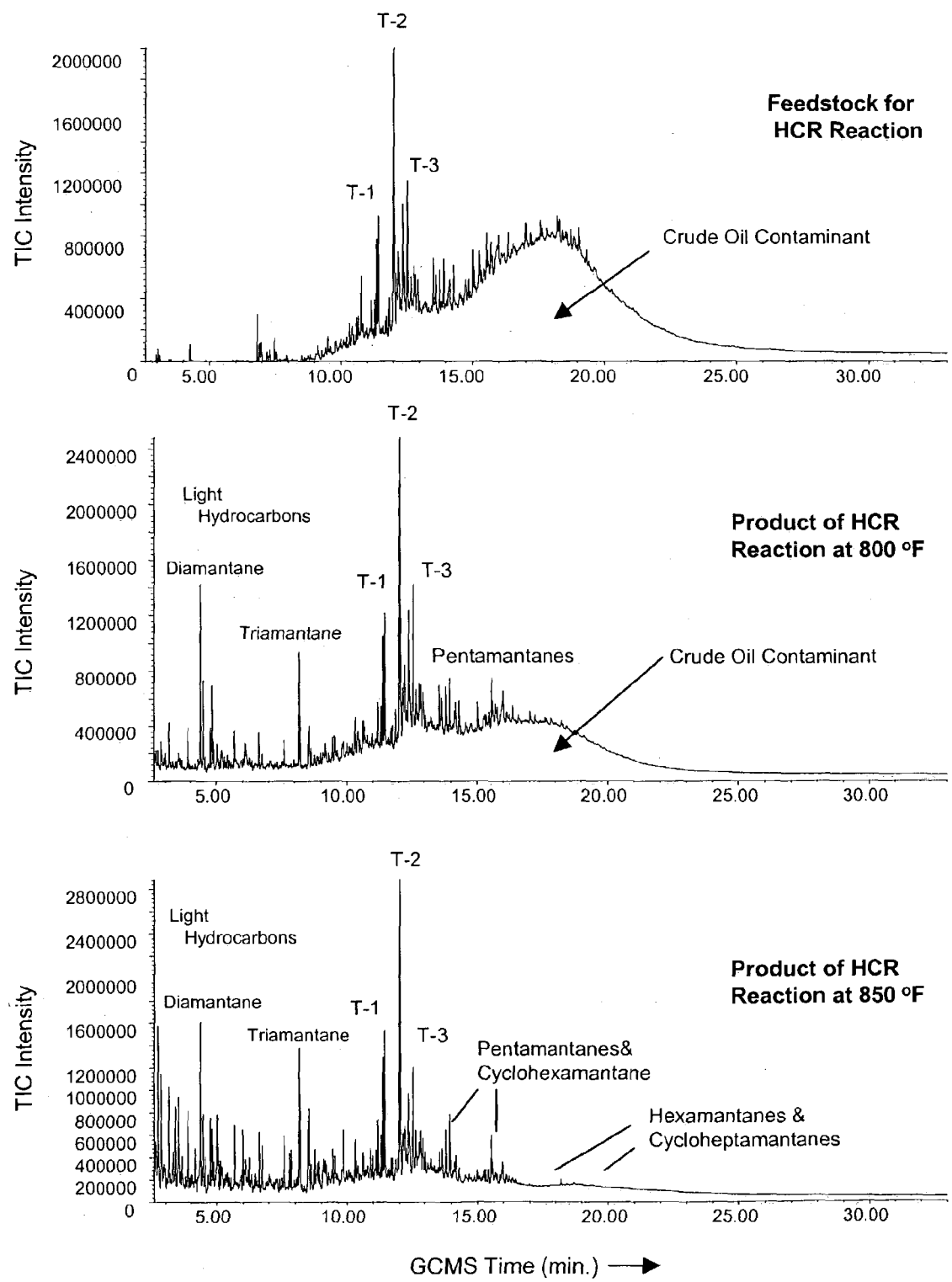
FIG. 5 provides three representative gas chromatographic-mass spectrometric (GCMS) total ion chromatograms (TIC) of (A) a higher diamondoid-containing fraction of a petroleum feed stock before hydroprocessing under conditions favoring hydrocracking and (B) and (C) the products of this hydroprocessing of the fraction at two different reaction temperatures. These chromatograms show that nondiamondoid components have been preferentially cracked and that tetramantanes, pentamantanes, hexamantanes and heptamantanes have become concentrated and available for isolation.

This distillate fraction contained tetramantanes, pentamantanes, and cyclohexamantane (and small amounts of other hexamantanes and certain heptamantanes) along with an undesirable crude-oil material as indicated in the gas chromatogram shown in FIG. 5A. This distillate fraction was then subjected to hydroprocessing in a laboratory scale continuous flow hydroprocesser using a catalyst containing USY zeolite, amorphous alumina and palladium at various temperatures, pressures, hydrogen flow rates and reactor space velocities.

In this hydroprocessing run, total pressure was maintained at 2300 psig, hydrogen flow rate at 5000 SCF/B, and reactor space velocity at 1.0 hr$^{-1}$, while the temperature was varied. FIGS. 5B and 5C are GCMS chromatograms of the liquid product from the hydroprocessing run. FIG. 5B is the data from the product produced at 800° F. reaction temperature showing that the broad nondiamondoid hydrocarbon peak drops in intensity relative to the higher diamondoid components when compared to the starting material (FIG. 5A). The best conversions were found with the reaction temperature at 850° F. as shown in FIG. 5C. At 850° F. nearly all of the undesirable nondiamondoid hydrocarbons boiling in the ~750° F. to ~850° F. have been converted and easily-removed lower molecular weight hydrocarbons. (FIG. 5C).

Figure 6:
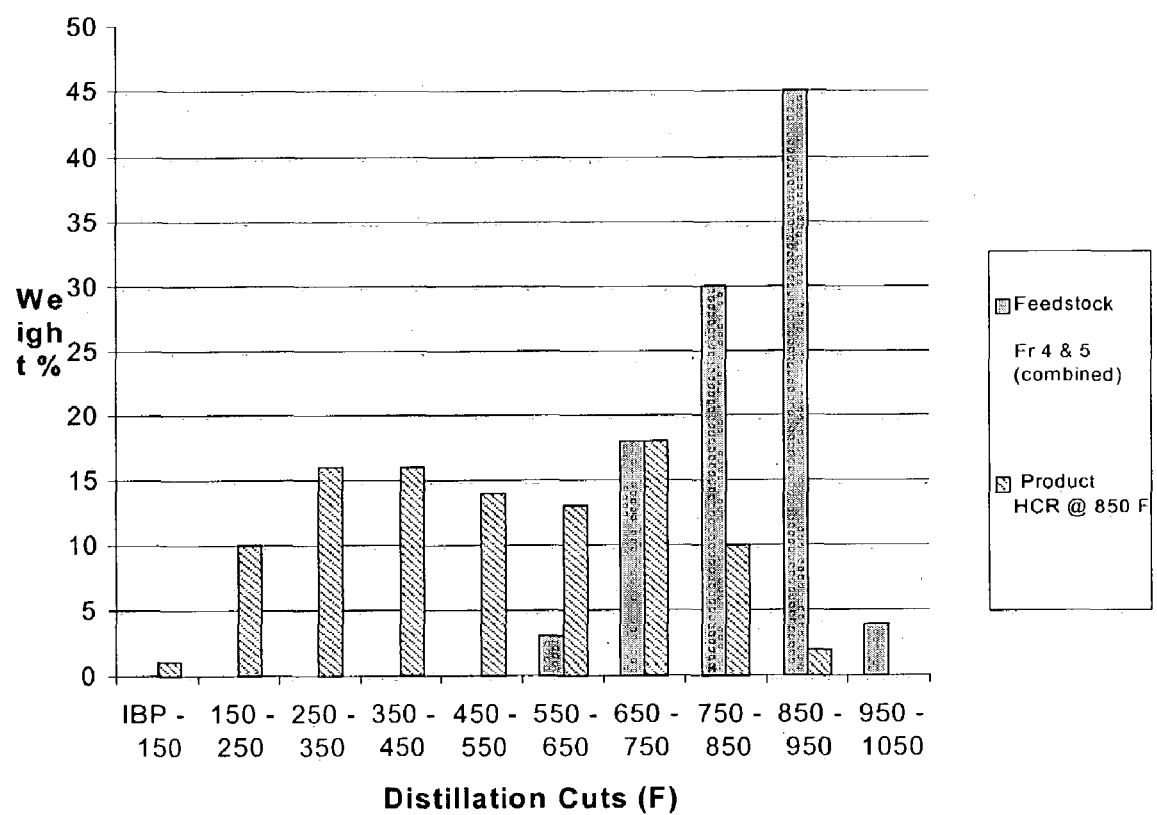
FIG. 6 is a bar graph showing yields of various distillate fractions determined by simulated distillation. Data are shown for both the hydroprocessing feedstock and the product produced at 850° F. reaction temperature. The graph shows the shift from higher boiling to lower boiling fractions brought about by the hydroprocessing reactions.

The shift from higher boiling to lower boiling material shown in FIGS. 5A through 5C is further illustrated from simulated distillation data shown in the bar graph in FIG. 6.

As can be seen from FIGS. 5B and 5C, and the bar graph of FIG. 6 the hydroprocessed product contains a large fraction of light hydrocarbons. These could be easily taken overhead such as by separator 20 and/or by fractionator 32 in FIG. 1 to permit the recovery and isolation of the higher diamondoids. Table 5 further describes the result of hydroprocessing at 850° F. reaction temperature.

TABLE 5

Results of Successful Hydroprocessing Runs on
Higher-Diamondoid Containing Feeds

| Temp, ° F. | 850 |
|---|---|
| WHSV | 1.69 |
| Total. P, psig | 1925 |
| Inlet H$_2$ P, psia | 1824 |
| Gas Rate, SCFB | 5191 |
| Conv < T, Wt % | 79.82 |
| Run Hour | 676 |
| No Loss Yields, Wt % | |
| Methane | 0.41 |
| Ethane | 2.03 |
| Propane | 4.17 |
| I-Butane | 1.43 |
| n-Butane | 2.32 |
| C5–180° F. | 9.29 |
| 180–250° F. | 8.5 |
| 250–550° F. | 38.88 |
| 550–700° F. | 17.42 |
| 700° F.+ | 18.44 |
| C5+ | 92.52 |
| Mass Closure, Wt % | 97.82 |
| TPG Dist, by Wt % | |
| St/5% | 76/194 |
| 10/30% | 232/358 |
| 50% | 487/ |
| 70/90% | 640/755 |
| 95/99% | 800/875 |

TABLE 6

Yields of Specific Higher Diamondoid Compounds in Feedstock and
Hydroprocessing Product at Reaction Temperature 850° F.

| Higher Diamondoid | Weight % in Feedstock | Weight % in Product 850° F. Reactor Temperature | Percent Yield |
|---|---|---|---|
| Methyltetramantane #1 | 0.26 | 0.54 | 208 |
| Tetramantane #1 | 0.27 | 0.71 | 264 |
| Tetramantane #2 | 0.96 | 1.76 | 182 |
| Tetramantane #3 | 0.46 | 0.65 | 142 |
| Methylpentamantane #1 | 0.20 | 0.17 | 85 |
| Pentamantane #1 | 0.34 | 0.34 | 91 |
| Pentamantane #2 | 0.29 | 0.27 | 94 |

Step 6—Removal of Aromatic and Polar Nondiamondoid Components

The product produced in Step 5 was passed through a silica-gel gravity chromatography column (using cyclohexane elution solvent) to remove polar compounds and asphaltenes (Step 6). The use of a silver nitrate impregnated silica gel (10 weight percent $AgNO_3$) provides cleaner diamondoid-containing fractions by removing the free aromatic and polar components. While it is not necessary to use this chromatographic aromatic-separation method, it facilitates subsequent steps.

Table 6 shows good yields for the pentamantane components and that the specified tetramantanes are actually being produced from other components during the process.

Step 7—Multi-Column HPLC Isolation of Higher Diamondoids

An excellent method for isolating high-purity higher diamondoids uses two or more HPLC columns of different selectivities in succession.

The first HPLC system consists of two whatman M20 10/50 ODS columns operated in series using acetone as mobile phase at 5.00 mL/min. A series of HPLC fractions were taken. Fractions were combined and taken for further purification on a second HPLC system.

Further purification of this combined ODS HPLC fraction is achieved using a Hypercarb stationary phase HPLC column which has a different selectivity in the separation of various higher diamondoids than the ODS column discussed above. Isolated diamondoids are analyzed for purity by GCMS and allowed to crystallize in a super-saturated solution in acetone.

EXAMPLE 2

Steps 1, 2 and 3 of Example 1 were carried out. Atmospheric residium of step 3 was then processed in a pilot-scale wiped film evaporator (U1C model KDLS).

In a first run, the step 3 residium was fed at a rate of 300 g/hr and a wiper speed of 300 rpm. Pressure was 0.004 millitorr and the average evaporate temperature was 127.5° C. This leads to a distillate fraction (65% by wt) having a nominal atmospheric boiling range of 650–750° F. and a residue (35% by wt) having a nominal boiling range at 750° F. The distillate contained 0.83% w sulfur, 397 wt ppm nitrogen and an API gravity of 11.3. The residue contained 2.71% w sulfur and had an API gravity of 12.3. The distillate of this run was used as "650–750° F. Feed" in this Example.

In a second run, the same step 3 residue was subjected to two stages of wiped film evaporation in the same evaporator and generally the same conditions. The first stage was carried out at an average temperature of 116° C. to yield a first stage distillate of 35% and first stage residue of 65%.

This residue was sent through a second stage at 147° C. to yield a second distillate (19.3% by wt, basis first stage feed) having a nominal boiling range of 750–850° F. This second distillate contained 6.92% w sulfur and had an API gravity of 15.2. This second distillate was used as "750–850° Feed" in this Example.

The 650–750° F. Feed was hydroprocessed under the following conditions on a Akzo-Nobel "Stars" KF848 base metal catalyst. This feedstock contained high levels of aromatics and significant levels of sulfur.

A total pressure of 2300 psi, LHSV of 1.0 $hrs^{-1}$, $H_2$/oil of 4000 scf/bbl and a temperature of 800° F. led to effective removal of undesirable non-higher diamondoid materials. However, measurable destruction of some of the higher diamondoids was observed.

A run at 730° F. at a LHSV of 0.25 $hrs^{-1}$ showed removal of the undesired specie but al less than full conversion.

Figure 9:
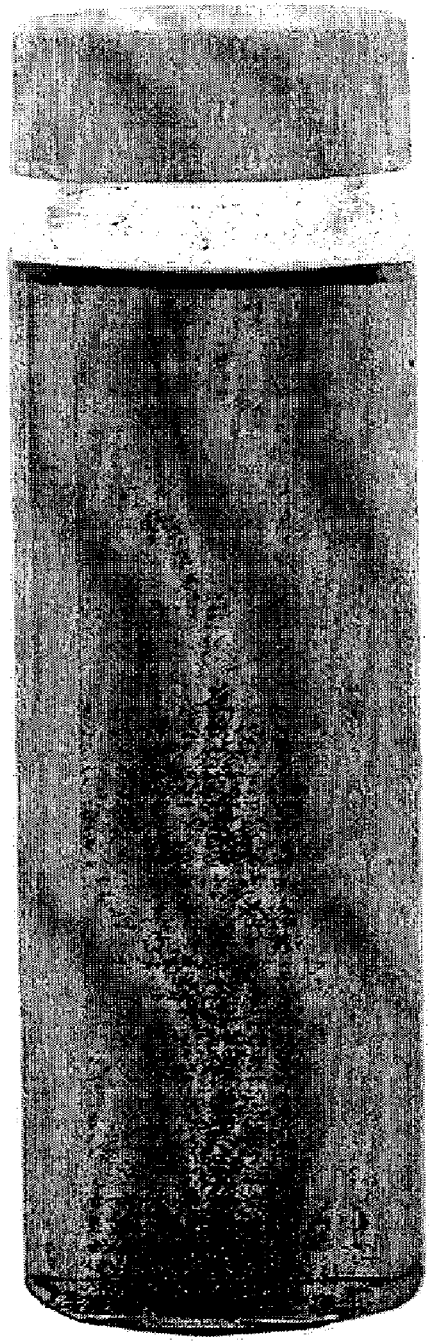
FIG. 9 is a black and white photo of feed and product samples illustrating that the product of the hydroprocessing has a very colorless appearance while the feed is deeply colored, indicative of aromatic compounds.
Figure 9:

A run at 760–780° F. and a LHSV of 0.25 $hrs^{-1}$ showed thorough conversion of nondiamondoids, particularly aromatics with lower levels of loss of desired higher diamondoids. The product was exceptionally clear (see FIG. 9) and free of coloration, carbon solids or tar.

Additional optimization runs were carried out using the 650–750° F. feed at 760° F., LHSV of 0.25 $hrs^{-1}$, 5000 scf/bbl, $H_2$/oil.

Representative higher diamondoids present in the feed and product are listed in Table 7.

TABLE 7

Yields of Specific Higher Diamondoid Compounds in Feedstock and Hydroprocessed Product

| Higher Diamondoid | Weight % in Feedstock | Weight % in Product Bottoms* | Percent Yield (wt-% of feed) |
|---|---|---|---|
| Methyltetramantane | 0.56 | 1.00 | 87 |
| Tetramantane #1 [1(2)3] | 0.66 | 1.32 | 96 |
| Tetramantane #2 [121] | 1.47 | 2.13 | 69 |
| Tetramantane #3 [123] | 0.41 | 0.61 | 72 |
| Pentamantane #1 | 0.05 | 0.10 | 93 |

*Bottoms equal 48 weight % of total hydroprocessed product.

Figure 7:
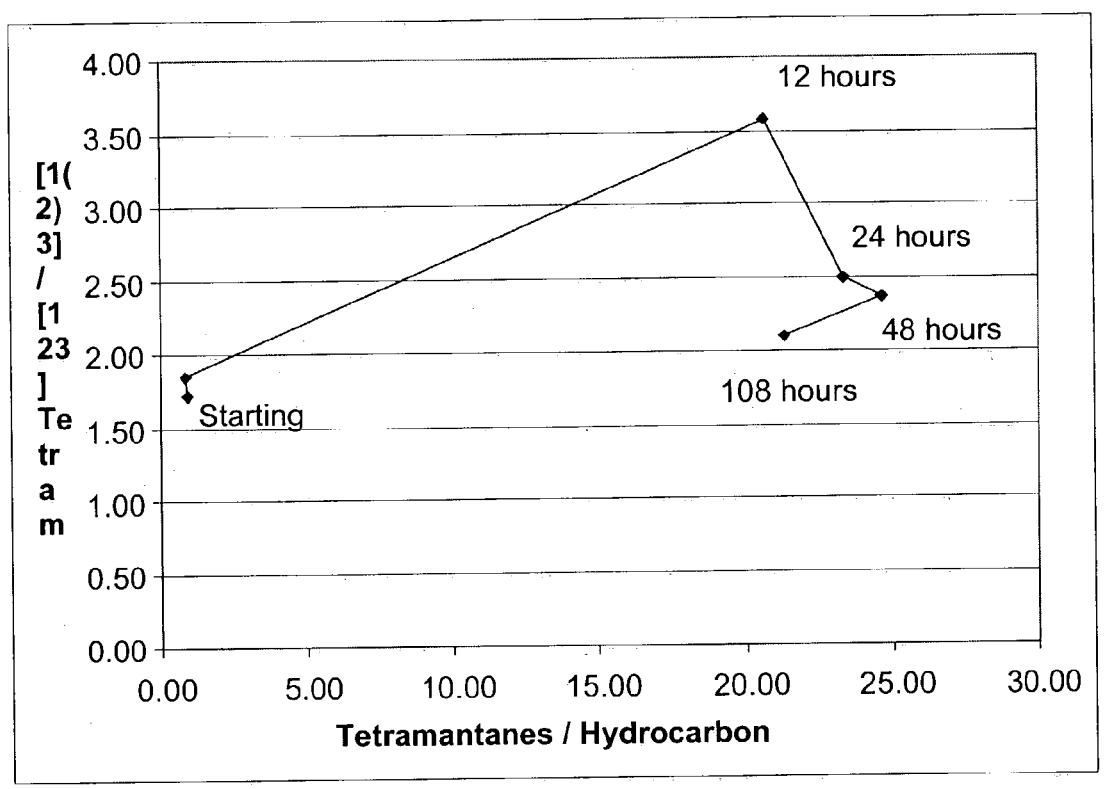
FIG. 7 is a graph showing how the degree of conversion of nondiamondoids can be varied but how the change in conversion can have an effect on the extent of destruction of higher diamondoids, as well.

FIG. 7 illustrates the results of studies on optimizing hydroprocessing conditions to destroy unwanted hydrocarbon impurities while retaining higher diamondoids. [1(2)3] tetramantane shows higher stability to processing than [123] tetramantane. An increase in the ratio of [1(2)3] to [123] tetramantane indicates the destruction of [123] tetramantanes relative to [1(2)3] tetramantane. Destruction of the unwanted hydrocarbon impurities is monitored using the ratio of the combined GCMS peak heights of the three tetramantanes to the combined GCMS peak heights of three selected impurities (9.20, 10.05 and 10.90 mins.—FIG. 8). The goal of the hydroprocessing is to maintain a constant ratio of [123] to [1(2)3] tetramantane (no destruction of [123] relative to [1(2)3], as an indicator of minimal destruction of higher diamondoids), while maximizing removal of hydrocarbon impurities as shown by a significant increase in the tetramantanes to hydrocarbon impurity peak ratio.

Figure 8:
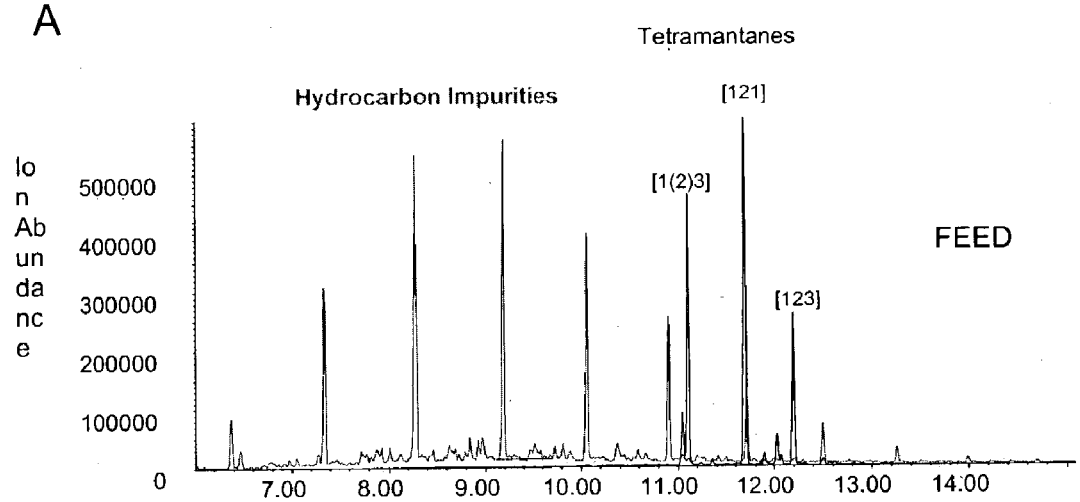
FIG. 8 provides GCMS selected ion chromatograms of a tetramantanes-containing fraction of a petroleum feedstock (A) before hydroprocessing under conditions leading to hydrocracking in combination with other hydroprocesses and (B) after such hydroprocessing.
Figure 8:
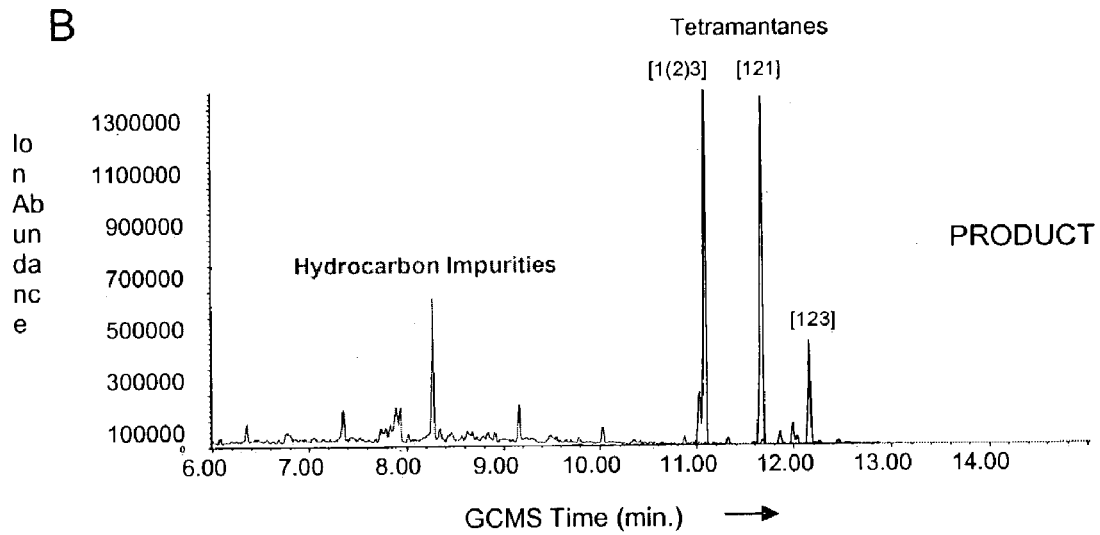

GCMS analyses were performed on the feed and product of these hydroprocessing runs and are shown in FIG. 8. These GCMS plots illustrate destruction of unwanted hydrocarbon impurities with retention of tetramantanes and other higher diamondoids. Mass spectral ion m/z 292 (the molecular ion of the tetramantane isomers) is used to illustrate the concentration of the tetramantane higher diamondoids. Mass spectral ion m/z 57 (fragment ion characteristic of a significant class of hydrocarbon impurities) is used as a measure of the concentration of unwanted impurities. FIG. 8A shows relative concentrations of tetramantanes and hydrocarbon impurities in the starting material. The hydrocarbon impurity peaks at 9.20, 10.05 and 10.90 minutes shown in FIGS. 8A and 8B were used to calculate parameters shown in FIG. 7 which illustrate destruction of hydrocarbon impurities (M/S=57 fragment ion) with retention of desired tetramantanes.

Figure 10:
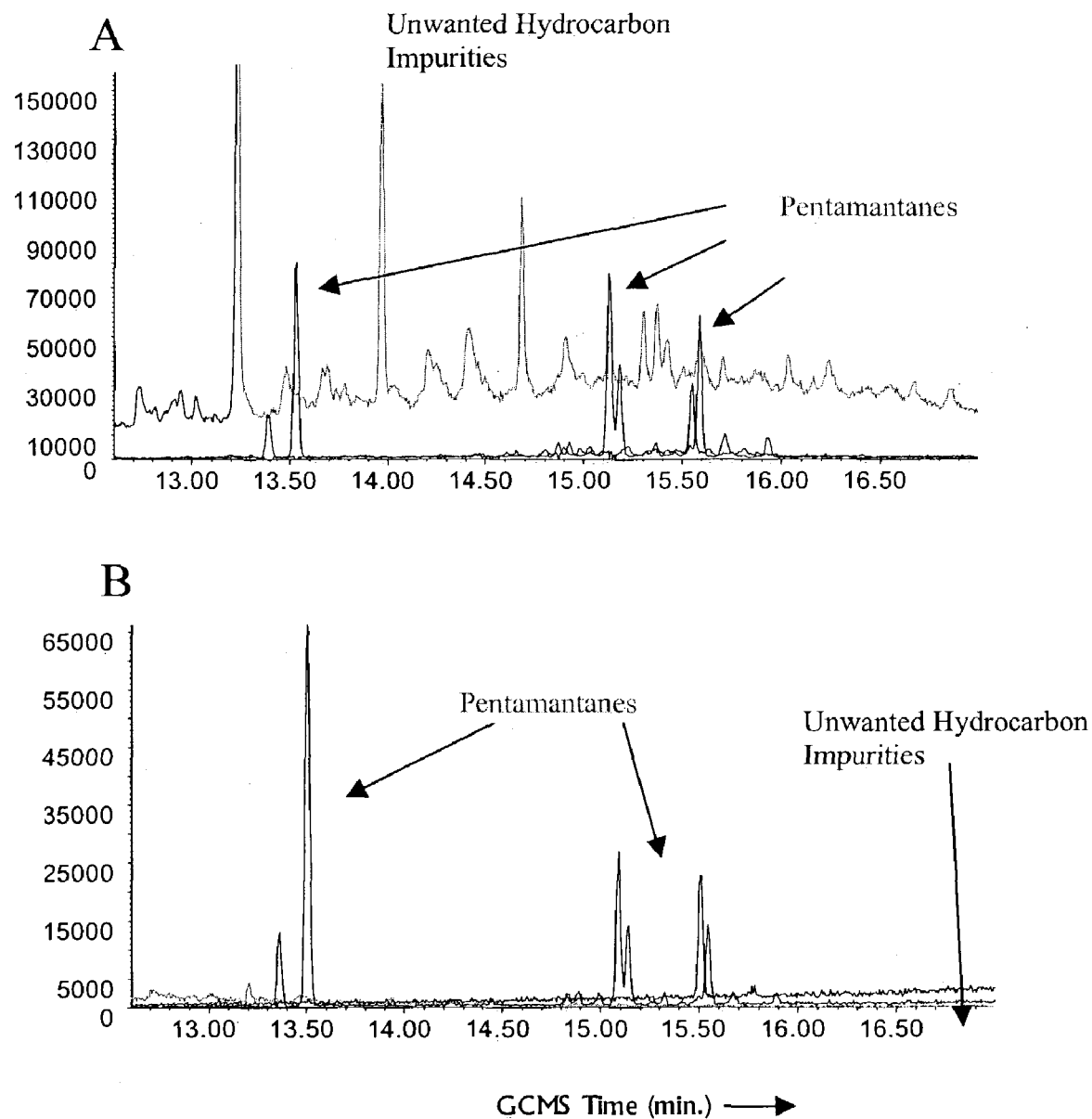
FIG. 10 provides GCMS selected ion chromatograms of a pentamantanes-containing fraction of a petroleum feedstock (A) before hydroprocessing and (B) after hydroprocessing under conditions leading to hydrocracking and other hydroprocesses.

Additional runs were carried out using the 750–850° Feed. This material contained over 6% w sulfur. When it was fed over the base metal catalyst under the general conditions listed in this example, three advantageous findings were observed. This cut processed similarly to the 650–750° cut. Aromatics present in the 750–850° cut were removed. The high sulfur content in the feed did not interfere with the desired hydroprocessing reactions. One predictable anomaly was observed and is shown in the diamondoid peak sizes in FIGS. 10A and 10B. Six diamondoid peaks were observed in the feed (A) and product (B). The two peaks at about 13.5 minutes, the two at about 15.1 minutes and the peak at about 15.52 minutes were determined to correspond to the 5 pentamantanes while the 15.48 minute peak corresponded to cyclohexamantane.

Cyclohexamantane has been previously observed to be exceptionally stable. 10 shows that it appears to be broken down to a less pronounced degree than at least most of the five pentamantanes. In all cases, however, the higher diamondoids are present in greatly enhanced concentrations in the hydroprocessing product, relative to similar-boiling other components in the feed.

What is claimed is:

1. A process for producing a composition enriched in higher diamondoids which process comprises:
    a) selecting a feedstock comprising recoverable amounts of higher diamondoids in admixture with nondiamondoid components;
    b) contacting the feedstock with hydrogen at a temperature of about 300 to about 950° F. and at an overall pressure of 200 to 4000 psi in the presence of a catalyst to preferencially react at least a portion of the nondiamondoid components therein to facilitate recovery of higher diamondoids from the reacted feedstock.

2. The process of claim 1 additionally comprising step c)
    c) recovering higher diamondoid(s) from the reacted feedstock.

3. The process of claim 1 wherein said contacting is hydroprocessing.

4. The process of claim 3 additionally comprising step c)
    c) recovering higher diamondoid(s) from the reacted feedstock.

5. The process of claim 3 wherein said hydroprocessing comprises hydrocracking.

6. The process of claim 5 additionally comprising step c)
    c) recovering higher diamondoid(s) from the reacted feedstock.

7. The process of claim 3 wherein said hydroprocessing comprises hydrotreating.

8. The process of claim 7 additionally comprising step c)
    c) recovering higher diamondoid(s) from the reacted feedstock.

9. The process of claim 1 wherein said contacting comprises hydrotreating followed by hydrocracking.

10. The process of claim 9 additionally comprising step c)
    c) recovering higher diamondoid(s) from the reacted feedstock.

11. The process of claim 1 wherein said contacting comprises hydrotreating and simultaneous hydrocracking.

12. The process of claim 11 additionally comprising step c)
    c) recovering higher diamondoid(s) from the reacted feedstock.

13. A process for recovering a composition enriched in higher diamondoids which process comprises:
    a) selecting a feedstock comprising recoverable amounts of higher diamondoids in admixture with nondiamondoid components;
    b) hydroprocessing the feedstock to convert at least a sufficient amount of nondiamondoid components therefrom to permit recovery of higher diamondoids from the hydroprocessed feedstock; and
    c) fractionating the hydroprocessed feedstock into lower boiling point fraction(s) enriched in converted nondiamondoid components and higher boiling fraction(s) enriched in higher diamondoids.

14. The process of claim 13 additionally comprising step d)
    d) recovering a fraction enriched in at least one higher diamondoid.

15. A process for recovering a composition enriched in higher diamondoids which process comprises:
    a) selecting a feedstock comprising recoverable amounts of higher diamondoids in admixture with nondiamondoid components;
    b) fractionating the feedstock to provide a fraction comprising recoverable amounts of higher diamondoids and nondiamondoid components; and
    c) contacting the feedstock fraction with hydrogen at a temperature of about 300 to about 950° F. and at an overall pressure of 200 to 4000 psi in the presence of a catalyst to react at least a portion of nondiamondoid components therein to facilitate recovery of higher diamondoids from the reacted feedstock fraction.

16. The process of claim 15 additionally comprising step d)
    d) recovering higher diamondoid(s) from the reacted feedstock fraction.

17. The process of claim 15 wherein said contacting is hydroprocessing.

18. The process of claim 15 wherein said contacting comprises hydrocracking.

19. The process of claim 15 wherein said contacting comprises hydrotreating.

20. The process of claim 15 wherein said contacting is hydrotreating followed by hydrocracking.

21. The process of claim 15 wherein said contacting comprises hydrotreating and simultaneous hydrocracking.

22. The process of claim 15 wherein the feedstock fraction is a distillation residue.

23. The process of claim 15 wherein the feedstock fraction is an overhead fraction.

24. The process of claim 15 wherein the process is a continuous process operating at space velocity of from 0.02 to 20 hrs$^{-1}$.

25. The process of claim 15 wherein the catalyst is a heterogeneous catalyst.

26. The process of claim 15 wherein the catalyst comprises noble metal.

27. The process of claim 15 wherein the catalyst comprises base metal.

28. The process of claim 15 wherein the catalyst comprises zeolite.

29. The process of claim 15 wherein the catalyst comprises silica or alumina, or silica-alumina.

30. The process of claim 15 wherein the space velocity is from about 0.02 to 20 hrs$^{-1}$ and the catalyst is a noble metal catalyst.

31. The process of claim 15 wherein the space velocity is 0.02 to 2.0 hrs$^{-1}$ the hydrogen circulation rate is from 200 to 20,000 scf/bbl of feed and the catalyst is a base metal catalyst.

* * * * *